United States Patent [19]

Bertoldi

[11] 4,245,987

[45] Jan. 20, 1981

[54] DENTAL ARTICULATOR

[75] Inventor: John J. Bertoldi, La Mirada, Calif.

[73] Assignee: Denar Corporation, Anaheim, Calif.

[21] Appl. No.: 5,772

[22] Filed: Jan. 23, 1979

[51] Int. Cl.³ ............................................. A61C 11/00
[52] U.S. Cl. ...................................................... 433/61
[58] Field of Search ................................... 433/61, 55

[56] References Cited

U.S. PATENT DOCUMENTS 1,041,270  10/1912  Gysi ....................................... 433/55

*Primary Examiner*—Robert Peshock
*Attorney, Agent, or Firm*—Edward D. O'Brian; K. H. Boswell

[57] ABSTRACT

Dental articulators have conventionally been constructed so as to utilize a lower assembly including a mandibular bow and an upper assembly including a maxillary bow connected together through the use of simulated condyles and fossa in such a manner as to permit movement between the two bows simulating the movement of the maxillary teeth relative to the mandibular teeth. The utility of such articulators can be improved through the use of a latch structure connecting the upper and lower assemblies in such a manner as to permit such movement and in such a manner as to permit the upper assembly to be moved into stable positions in which the maxillary bow extends substantially vertically from the mandibular bow and in which the maxillary bow and the mandibular bow both face upwardly.

5 Claims, 9 Drawing Figures

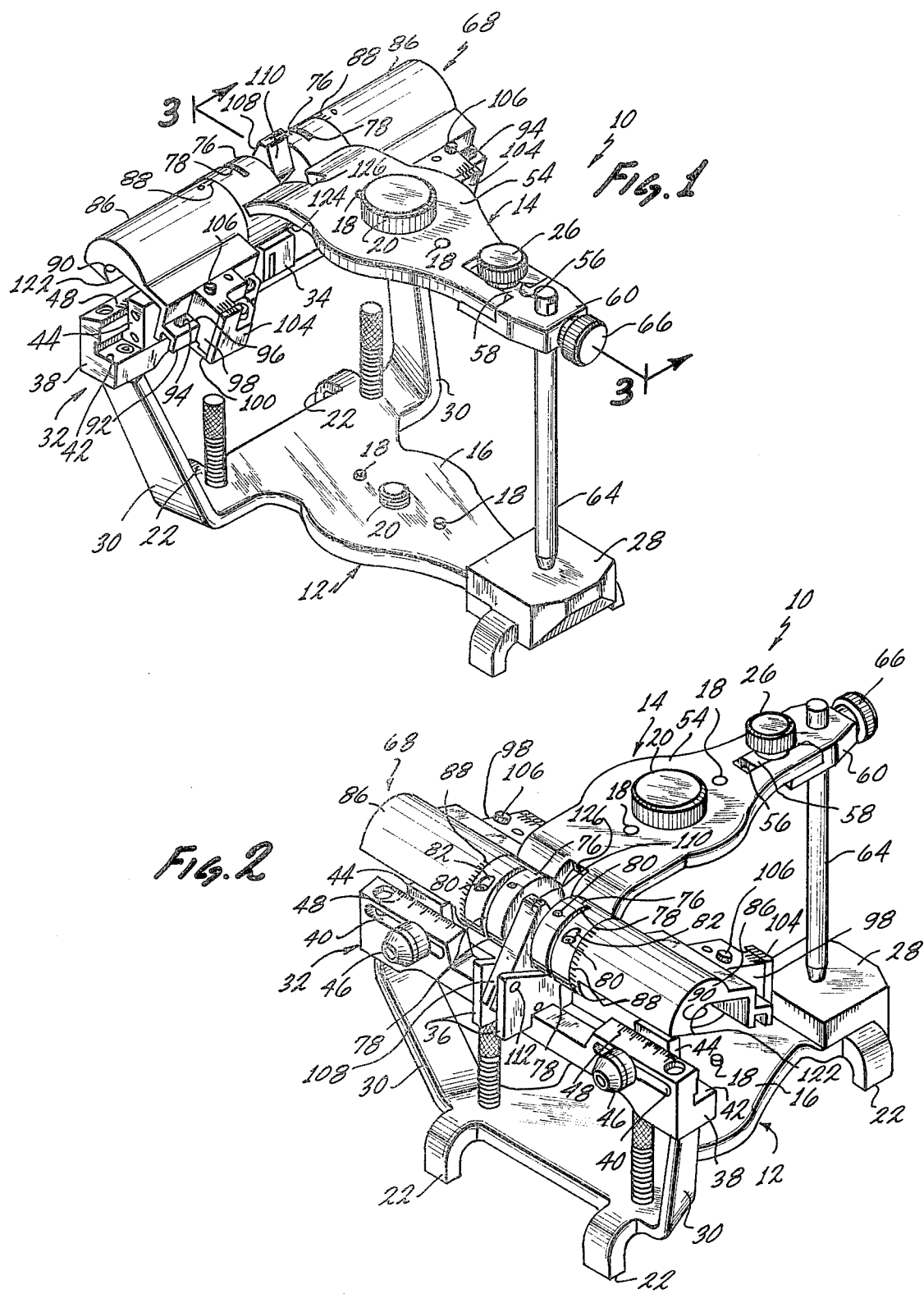

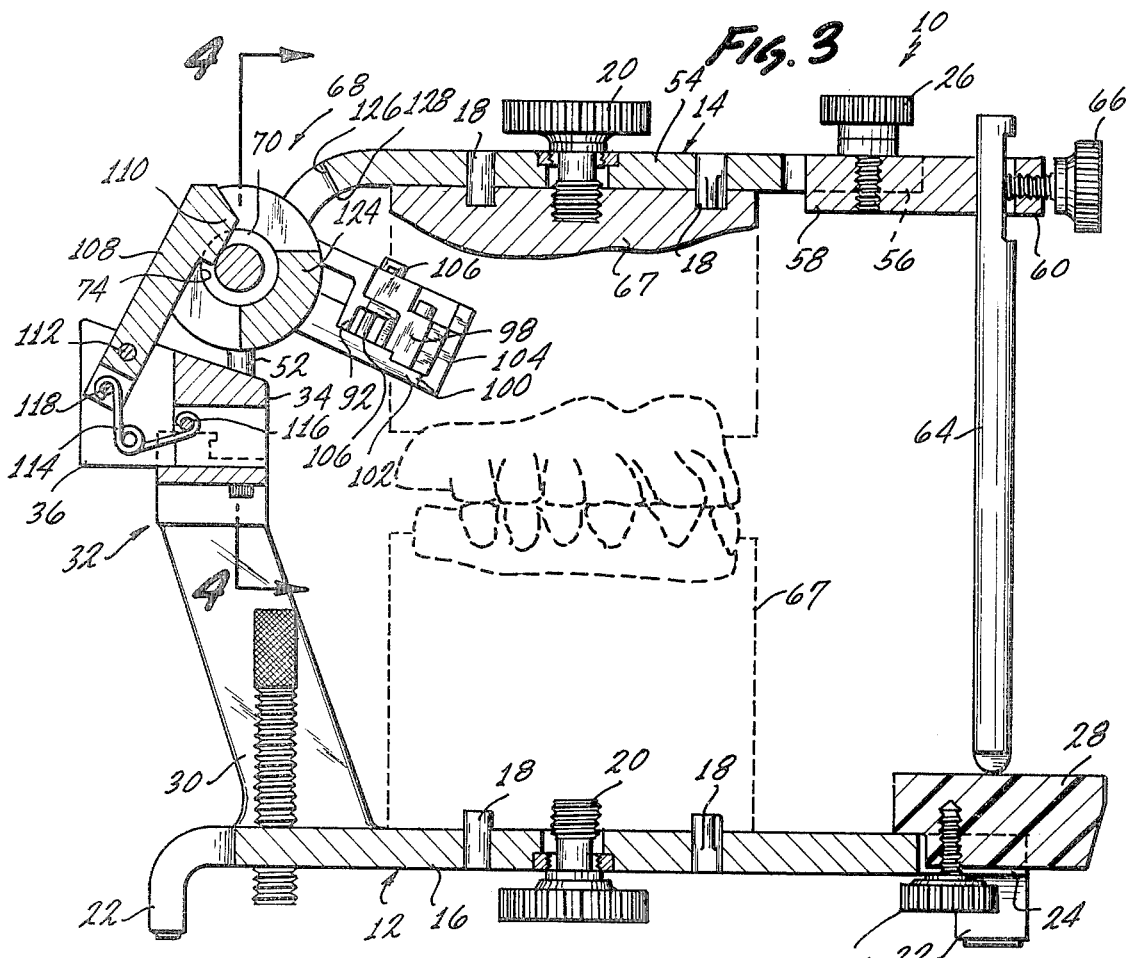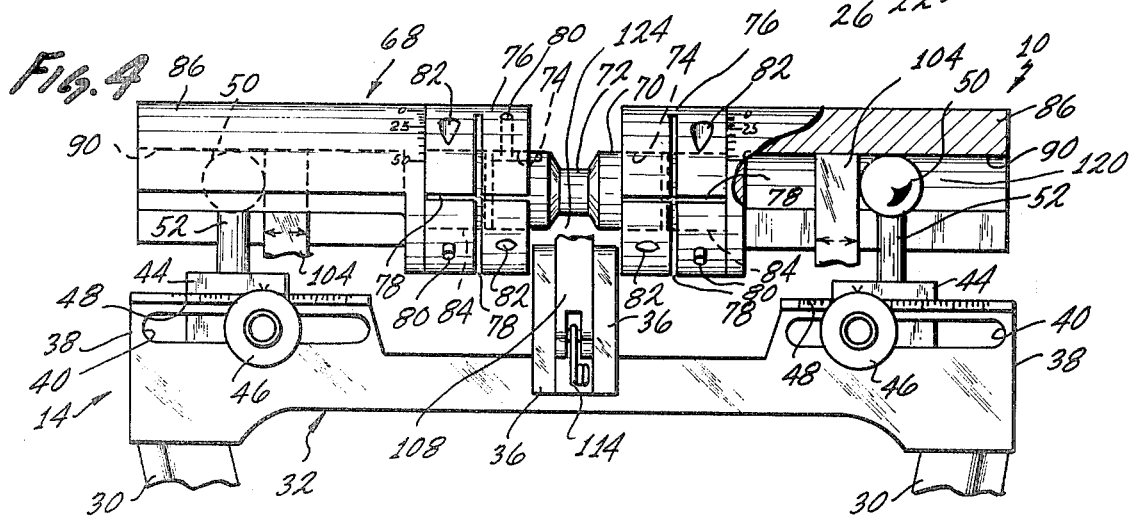

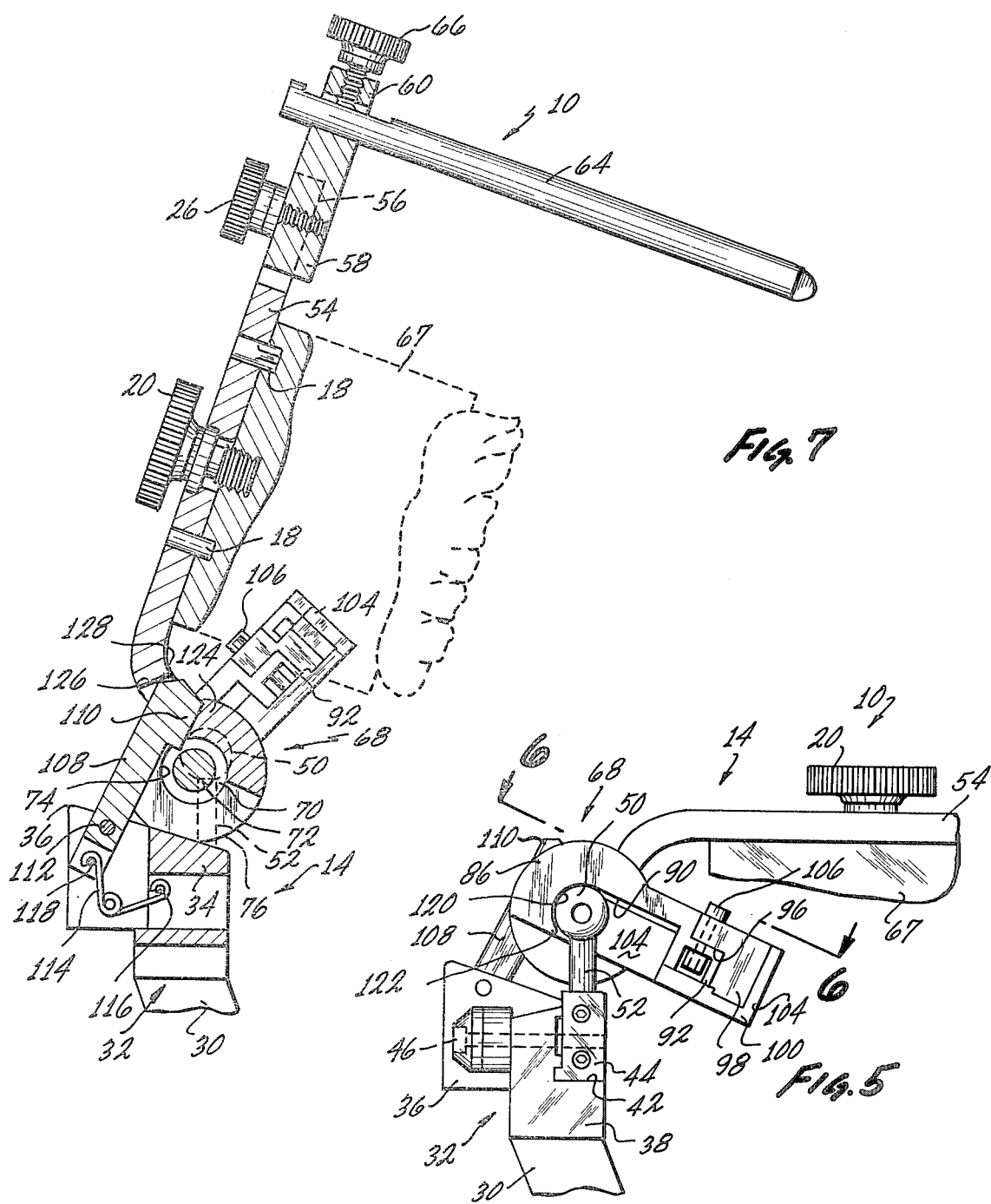

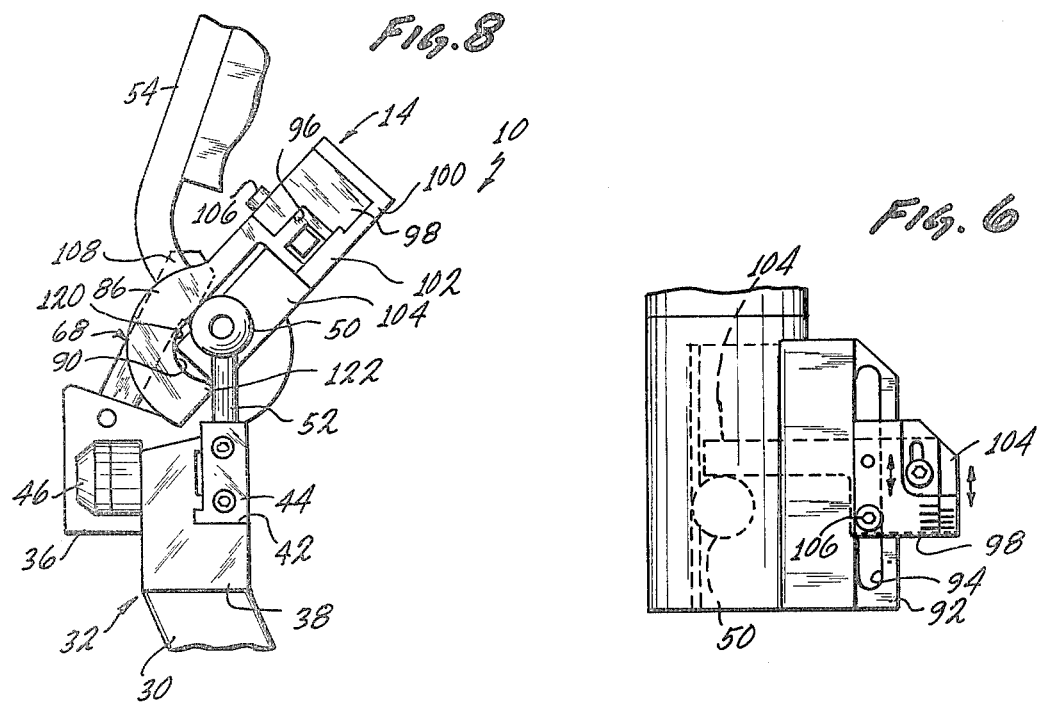
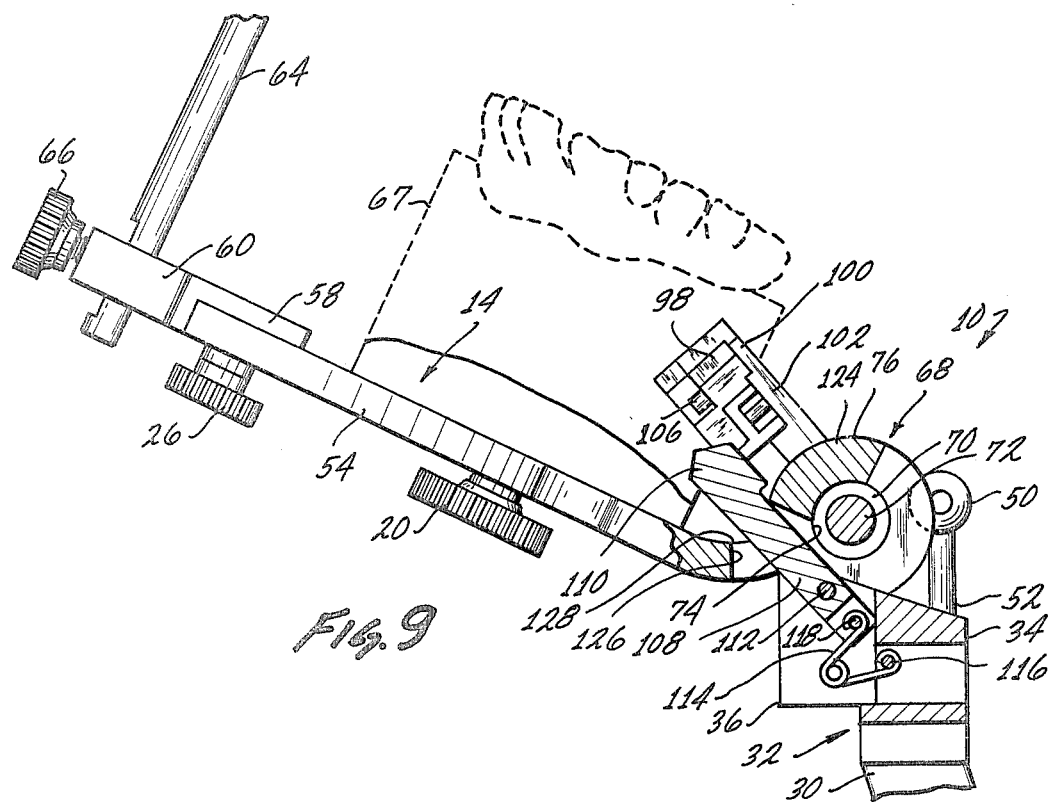

DENTAL ARTICULATOR

BACKGROUND OF THE INVENTION

The invention set forth in this specification pertains to new and improved dental articulators and more particularly to dental articulators which are more desirable than prior related articulators in that they can be manipulated into various positions facilitating work on dental casts or the like.

The term "articulator" is commonly utilized in the dental field to designate any of a wide variety of differently constructed and differently appearing devices for use in obtaining articulation corresponding to the articulation between maxillary and mandibular teeth of a particular individual. These devices have normally been constructed so as to utilize two principal assemblies or parts—a lower assembly and an upper assembly. The lower assembly in conventional articulators normally includes a plate-like structure commonly referred to as a mandibular bow which is adapted to hold and support simulated mandibular teeth while the upper assembly in a conventional articulator normally includes a corresponding plate-like structure commonly referred to as a maxillary bow which is adapted to hold or support simulated maxillary teeth.

Normally these assemblies are constructed so that the lower assembly includes a lower cross-member and the upper includes an upper cross-member. In a conventional articulator simulated condyle elements are located on one of these cross-members while simulated fossa elements are located on the other of these cross-members in engagement with the simulated condyle elements. These fossa elements are normally constructed so that such engagement permits conventional centric rotation, lateral movement and protrusive movement between the two assemblies corresponding to such rotation and movement of a human jaw.

It is not considered that an understanding of the present invention requires a more detailed description of various prior dental articulators. In spite of the fact that such articulators have been constructed in a number of different ways, as for example, to improve the ease of their use by a dentist, it is considered that there still exists a need for improvement in the construction of dental articulators. More specifically it is considered that there is a need for articulators which are constructed not only in such a manner as to simulate movement of maxillary teeth relative to mandibular teeth but which are also constructed in such a manner that simulated teeth held by the bows of an articulator can be located in various different positions with respect to one another so as to facilitate various operations as are performed by a dentist in utilizing an articulator.

SUMMARY OF THE INVENTION

A broad or basic object of the present invention is to provide new and improved articulators which are intended so as to fulfill this need. Related objects of the present invention are to provide articulators which are not significantly more expensive to construct than prior articulators, which may be easily and conveniently utilized in various different ways as may be desired during their use, and which are capable of reliably operating over a prolonged period with minimal maintenance. A further objective of the invention is to provide for new and improved articulators which are constructed in such a manner as to permit the fossa and condyle elements used in such articulators to be separated from one another in order to permit the upper assembly in such an articulator to be moved to various positions facilitating the performance of various operations on simulated teeth held by the articulator.

In accordance with this invention these various objectives are achieved by providing a dental articulator having a lower assembly and an upper assembly, said lower assembly including a lower mandibular bow and a connected lower cross-member, said upper assembly including an upper maxillary bow and a connected upper cross-member, one of said cross-members carrying two simulated condyle means, the other of said cross-members carrying two simulated fossa means, said fossa means engaging said condyle means so as to permit movement of said maxillary bow relative to said mandibular bow simulating movement of the maxillary teeth relative to mandibular teeth, one of said cross-members carrying a latch means engaging the other of said cross-members for holding said upper and lower assemblies relative to one another with said condyle means and said fossa means in engagement with one another in such a manner as to permit such movement in which the improvement comprises: said latch means being capable of holding said assemblies relative to one another in a position in which said maxillary bow extends substantially vertically from said mandibular bow and in another position in which said maxillary bow and said mandibular bow both face upwardly.

BRIEF DESCRIPTION OF THE DRAWING

The invention described in this specification is best more fully explained with reference to the accompanying drawings in which:

FIG. 1 is an isometric view showing the front, the top and a side of a presently preferred embodiment or form of an articulator in accordance with this invention;

FIG. 2 is an isometric view of the articulator shown in FIG. 1 showing the rear of this articulator;

FIG. 3 is a cross-sectional view taken at line 3—3 of FIG. 1 in which various parts of the articulator are shown in elevation;

FIG. 4 is a rear elevational view of a part of the articulator shown in the preceding figures in which parts are shown in section at line 4—4 of FIG. 3;

FIG. 5 is a partial side elevational view of the articulator shown in FIG. 1;

FIG. 6 is a partial cross-sectional view taken at line 6—6 of FIG. 5;

FIG. 7 is a partial cross-sectional view corresponding to FIG. 3 but with the upper assembly of the articulator in a position in which the maxillary bow of this assembly extends substantially vertically relative to the mandibular bow on the lower assembly;

FIG. 8 is a partial side elevational view corresponding to FIG. 5 showing the upper assembly in the same position in which it is shown in FIG. 7; and FIG. 9 is a partial cross-sectional view corresponding to FIG. 7 in which the upper assembly is in a position in which both the maxillary and mandibular bows face upwardly, a portion of this figure being shown in elevation for convenience of illustration.

The precise articulator illustrated is constructed so as to utilize the concepts and principles of the invention set forth in the appended claims forming a part of this disclosure. Those skilled in the field of the design and construction of dental articulators will realize that these concepts or principles may be easily utilized in other articulators differing from the precise articulator illustrated in various known manners and differing from the precise articulator illustrated as to various matters of routine design or engineering skill.

DETAILED DESCRIPTION

In the drawing there is shown an articulator 10 in accordance with this invention which is constructed so as to include a lower assembly 12 and an upper assembly 14. This lower assembly 12 is provided with a mounting plate or mandibular bow 16. This bow 16 carries conventional alignment pins 18 and a conventional mounting screw 20. This bow 16 is normally supported by means of legs 22. Preferably the bow 16 is constructed adjacent to its front (not separately numbered) so as to include an elongated slot 24 utilized in connection with another screw 26 in mounting an incisal table 28 on the lower assembly 12.

Toward the rear of the bow 16 there are located two upstanding arms 30 which carry an elongated, generally linear lower cross-member 32. This lower cross-member 32 carries an upstanding bifurcated mounting block 34 having spaced, parallel bifurcations or walls 36 extending transverse to the length of the cross-member 32. This cross-member 32 is also provided with upstanding mounting walls 38 which are spaced equidistant from the block 34. These walls 38 are provided with elongated slots 40 and are located generally alongside and parallel to what may be loosely regarded as a linear track 42 extending along the length of the cross-member 32 beneath the block 34.

Sliding blocks 44 are located on the track 42 adjacent to each of the walls 38 and are adapted to be secured to the walls 38 at various distances from the block 34 through the use of conventional screws 46. Small scales 48 may be located on the mounting walls 38 for use in ensuring that the blocks 44 are mounted so that the distance between simulated condyles or condylar elements 50 is as desired during the use of the articulator 10. These condyle elements 50 are of a conventional spherical shape and are mounted on the blocks 44 through the use of rods 52.

The upper assembly 14 is constructed so as to include a mounting plate or maxillary bow 54 carrying pins 18 and a screw 20 as previously described. This maxillary bow 54 is also provided with a slot 56 which is approximately above the slot 24 when the articulator 10 is in a closed position as indicated in FIGS. 1, 2 and 3. This slot 56 is adapted to receive a projection 58 on a holder 60 so as to ensure correct positioning of this holder 60 relative to the bow 54. This holder 60 is conveniently secured in place by another screw 26 corresponding to the screw 26 previously described.

This holder 60 includes an opening 62 in which there is slidably fitted an incisal pin 64. This pin 64 is normally held against movement by the use of another screw 66 so that the incisal pin 64 rests against the incisal table 28 so as to support a part of the weight of the upper assembly 14 when the articulator 10 is in a closed position as shown in FIGS. 1 to 3. In this closed position casts 67 as indicated in phantom in FIGS. 3, 7 and 9 are located opposite one another.

This maxillary bow 54 carries an upper cross-member 68 which is normally located above, adjacent to and parallel to the lower cross-member 32 as shown. Although it is possible to construct the upper cross-member 68 so that it essentially is one elongated unitary part it is considered preferable to construct it of a series of parts as hereinafter described. The centermost of such parts is a centrally located shaft 70 having a necked down, centrally located groove 72 serving as a latch guide. The opposed extremities of this shaft 70 (not separately numbered) are fitted within openings 74 in generally cylindrical mounting cylinders 76.

These cylinders 76 are provided with axially and transversely extending slots 78. With this structure the shaft 70 can conveniently be clamped within the cylinders 76 through the use of screws 80 extending through openings 82. Similarly the other screws 80 in other openings 82 may be utilized to clamp short shafts 84 in the openings 74. These shafts 84 extend from retainers 86. This structure permits other small scales 88 on the cylinders 76 to be utilized in adjusting for the protrusive angle.

The retainers 86 are provided with elongated, aligned, hollowed out, somewhat socket-like channels 90 which are utilized as to in effect form parts of simulated fossa elements (not separately identified) in accordance with the invention. These retainers 86 are preferably formed integrally with elongated forwardly extending, downwardly directed U shaped rails 92, each of which is provided with an elongated slot-like opening 94. Notches 96 in mounting blocks 98 are located against the rails 92. These blocks 98 are positioned against support walls 100 carried by a plate 102. This plate 102 in turn carries upwardly extending limiting walls 104 which fit within the socket-like channels 90.

Screws 106 are used in connection with the plate 102 and the mounting blocks 98 for the purpose of adjustably mounting the blocks 98, the plate 102 and the limiting walls 104 upon the retainers 96. This structure permits the limiting walls 104 to be adjusted with respect to the simulated condyle elements 50 and permits an adjustment to be made between the position of each block 98 and its associated plate 102 in fitting the condyle elements 50 into the channels 90 alongside the plate 102 in such a manner as to effectively simulate immediate side shift within a jaw during the use of the articulator 10.

During the use of this articulator 10 the upper assembly 14 is normally held on the lower assembly 12 through the use of a small latch arm 108 having a hooked end 110. This latch arm 108 is pivotally mounted between the walls 36 on the block 34 by means of a small pivot pin 112 so as to rotate in a plane transverse to a line (not shown) drawn between the centers of the simulated condyle elements 50 and generally transverse to the length of the lower cross-member 32. A conventional so-called hairpin-type spring 114 is located between these walls 36 and is attached to the block 34 by means of another pin 116 and is attached to the arm 108 by means of a further pin 118.

This spring 114 is located as shown so that it will bias the latch arm 108 into a position as indicated in FIG. 3 when the articulator 10 is in a closed position. In this closed position the latch arm 108 fits in the groove 72 so as to exert a force component tending to hold the upper assembly 14 so that the simulated condyle elements 50 are seated within the socket-like channels 90 in contact with the curved rear ends 120 of these channels 90. When the articulator 10 is in this closed position the bows 16 and 54 are located substantially parallel to one another. This structure permits the entire upper assembly 14 to be rotated from this closed position as shown in FIGS. 1 to 3 to a substantially ninety degree open position as indicated in FIG. 7 of the drawing in which the bows 16 and 54 are located at nearly a right angle to one another.

During such rotation the upper cross-member 68, of course, rotates upon the simulated condyle elements 50 until such time as edges 122 of the rear ends 120 hit against the rods 52. This is indicated in FIG. 8 of the drawing. As this occurs further movement of the upper assembly 14 from a closed position as shown in FIG. 3 toward a position as shown in FIG. 7 will result in the condyle elements 50 sliding within the channels 90 to positions as shown in FIG. 8 so as to be spaced from the rear ends 120. During the movement of the upper assembly 14 as indicated a connecting segment 124 extending between the cylinders 76 will abut against the latch arm 108 so as to pivot this latch arm 108 to a limited extent against the biasing action of the spring 114. As this occurs the latch arm 108 will be moved upwardly through what may be referred to as a notch 126 in the maxillary bow 54 immediately adjacent to the upper cross-member 68.

As the latch arm 108 is moved in this manner it will be directed upwardly to an increasing extent so as to project through the notch or opening 126 until such time as it is located generally between an undersurface or wall 128 and the segment 124. In this position the spring 114 will tend to hold the arm 108 against movement while concurrently gravity holds the upper assembly 14 against this arm 108 so as to in turn hold the arm 108 against the segment 124. In this position the upper assembly 14 will be reasonably stabilized against movement by contact of the rear edges 122 against the rods 52.

With the articulator 10 the upper assembly 14 can be moved out of the substantially ninety degree position as shown in FIG. 7 to a closed position as indicated in FIGS. 1 to 3 by generally lifting or pulling the upper assembly 14 away from the lower assembly 12 so as to move the simulated condyle elements 50 within the channels 90 back against the rear ends 120 so that the upper assembly 14 may be pivoted downwardly. During such movement the latch arm 108, of course, moves in the reverse of the manner described in the preceding so as to engage the groove 72 in the shaft 70 in order to bias the upper assembly 14 in a closed position.

The articulator 10 is considered to be particularly desirable in that the upper assembly 14 can be moved from a position as indicated in FIG. 7 to a position as indicated in FIG. 9 in which both of the bows 16 and 54 face upwardly by the simple expedient of rotating the upper assembly 14 relative to the lower assembly 12 from the position as shown in FIG. 7 to a position as indicated in FIG. 9. As this occurs the upper cross-member 68 will be moved to a position in which it can be described as resting upon the lower cross-member 32. Also as this occurs the channels 90 will be moved so that the simulated condyle elements 50 do not engage these channels 90. Further, as this occurs movement of the upper assembly 14 generally away from the lower assembly 12 will be prevented by engagement of the latch arm 108 with the connecting segment 124 as indicated in FIG. 9. This latch arm 108 is preferably dimensioned as shown so that it can only rotate to a position as indicated in FIG. 9 from a position as indicated in FIG. 7 so as to limit movement of the upper assembly 14. In the FIG. 9 position the latch arm 108 abuts against the block 34 and in effect "hooks" the segment 124 so as to hold the upper cross-member 68 generally against the lower cross-member 32.

It is considered that the articulator 10 is advantageous in that the upper assembly 14 can be moved to a position as shown in FIG. 9 through the action indicated in the preceding. In this position both of the bows 16 and 54 in effect face substantially the same direction so as to be easily accessible. This facilitates the performance of work on simulated teeth such as may be carried by these bows 16 and 54. After the performance of such work the upper assembly 14 may be returned to a closed position by first rotating it to a position as indicated in FIG. 7. This has the effect of pivoting the upper assembly 14 so that the condyle elements 50 are again located generally within the channels 90. When the upper assembly 14 is in this intermediate position as indicated in FIG. 7 the upper assembly 14 may be manipulated as indicated in the preceding so that it can be further rotated to a closed position.

It is believed that it will be obvious from a consideration of the drawing how the upper assembly 14 may also be removed from the lower assembly 12. This may be accomplished by simply manipulating the latch 108 so that the upper assembly 14 may be lifted off the lower assembly 12.

One aspect of the articulator 10 is considered to be of an unusual, significant character. This relates to the manner in which this articulator 10 is constructed so as to permit "normal" articulation between the lower and upper assemblies 12 and 14 while still permitting the upper assembly 14 to in effect be pivoted to a greater extent than is possible with a normal construction involving simulated condyles and fossa. Normally only a limited amount of pivoting is permissible between simulated fossa and condyles because of the geometry of the parts involved. The particular articulator 10 described permits a significant amount of relative movement by permitting sliding of the simulated condyles 50 in the channels 90 and by permitting disengagement of these simulated condyles 50 from these channels 90 when the upper assembly 14 is in open positions as indicated.

I claim:

1. A dental articulator having a lower assembly and an upper assembly, said lower assembly including a lower mandibular bow and a connected lower cross-member, said upper assembly including an upper maxillary bow and a connected upper cross-member, one of said cross-members carrying two simulated condyle means, the other of said cross-members carrying two simulated fossa means, said fossa means engaging said condyle means so as to permit movement of said maxillary bow relative to said mandibular bow simulating movement of the maxillary teeth relative to mandibular teeth, one of said cross-members carrying a latch means engaging the other of said cross-members for holding said upper and lower assemblies relative to one another with said condyle means and said fossa means in engagement with one another in such a manner as to permit such movement in which the improvement comprises:

said latch means comprising a latch member pivotally mounted on said lower cross-member, said latch member having an extremity extending generally toward said maxillary bow, said upper cross-member including a shaft located adjacent to said extremity of said latch member and an opening extending through said upper cross-member adjacent to said shaft, said opening including two opposed walls, said extremity of said latch member engaging said shaft when said maxillary bow is in a position substantially parallel to said mandibular bow, one of said walls of said opening being capable of abutting against said latch member as said maxillary bow is rotated from said substantially parallel position to said mandibular bow to a position in which said maxillary bow extends substantially vertically with respect to said mandibular bow so as to pivot said extremity of said latch member within said opening in engagement with said walls of said opening in a position in which such engagement will hold said maxillary bow against movement caused by gravity, said condyle means are capable of movement away from said fossa means in order to permit movement of said maxillary bow from said substantially vertical position to a position in which said maxillary bow faces upwardly on the side of said lower member remote from said mandibular bow, said latch member being capable of moving through said opening as said maxillary bow is moved from said substantially vertical position to said upwardly facing position and being capable of engaging said upper cross-member so as to hold said maxillary bow in said upwardly facing position.

2. A dental articular as claimed in claim 1 including:

spring means connecting said latch member and said lower cross-member for biasing said extremity of said latch member generally against said upper cross-member.

3. A dental articular having a lower assembly and an upper assembly, said lower assembly including a lower mandibular bow and a connected lower cross-member, said upper assembly including an upper maxillary bow and a connected upper cross-member, one of said cross-members carrying two simulated condyle means, the other of said cross-members carrying two simulated fossa means, said fossa means engaging said condyle means so as to permit movement of said maxillary bow relative to said mandibular bow simulating movement of the maxillary teeth relative to mandibular teeth, one of said cross-members carrying a latch means engaging the other of said cross-members for holding said upper and lower assemblies relative to one another with said condyle means and said fossa means in engagement with one another in such a manner as to permit such movement in which the improvement comprises:

said condyle means are located on said lower cross-member and said fossa means are located on said upper cross-member, said condyle means are capable of being separated from said fossa means, said latch means being capable of holding said assemblies relative to one another in a position in which said maxillary bow extends substantially vertically from said mandibular bow and in another position in which said maxillary bow and said mandibular bow both face upwardly, said latch means comprises a hooked arm pivotally mounted on said lower cross-member and three parts on said upper cross-member, a first of said parts comprising a shaft located on said upper cross-member, the second of said parts comprising a wall attached to said upper cross-member, the third of said parts comprising a segment means on said upper cross-member, said arm engaging said shaft when said articulator is in a closed position in which said bows are opposite one another, said condyle means being engaged by said fossa means in said closed position, said arm engaging said wall and said segment means so as to support said upper assembly against movement due to the action of gravity when said upper assembly is in said substantially vertical position, the hook on said arm engaging said segment means so as to limit movement of said upper assembly away from said lower assembly when said upper assembly is in said upwardly facing position, and said fossa means are moved out of engagement with said condyle means during movement of upper assembly from said substantially vertical position to said upwardly facing position.

said arm engaging said segment means so as to hold said upper cross-member against said lower cross-member in said upwardly facing position.

4. A dental articulator as claimed in claim 3 wherein:

there is an opening in said upper assembly generally between said upper cross-member and said upper bow, said wall and said segment means are located on opposite sides of said opening and said shaft is located adjacent to said opening, said arm is shaped so that during movement of said upper assembly from said closed position to said substantially vertical position said segment engages said arm so as to deflect said arm so as to cause said arm to move through said opening into a position in which said wall rests against said arm and moves said arm into contact with said segment means, said segments means being capable of engaging said arm so as to pivot said arm to a position in which said segment means is engaged by said arm so as to prevent further movement of said upper assembly relative to said lower assembly as said upper assembly is rotated from said substantially vertical position to said upwardly facing position.

5. A dental articulator as claimed in claim 4 wherein:

said arm is pivotally mounted on said lower assembly, and said latch means includes spring means normally biasing said arm generally toward said shaft means and said segment means.

* * * * *